(12) United States Patent
Torstensen

(10) Patent No.: US 9,889,272 B2
(45) Date of Patent: Feb. 13, 2018

(54) LIQUID STOP

(71) Applicant: Coloplast A/S, Humlebaek (DK)

(72) Inventor: Jan Torstensen, Virum (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/363,418

(22) PCT Filed: Dec. 7, 2012

(86) PCT No.: PCT/DK2012/050451
§ 371 (c)(1),
(2) Date: Jun. 6, 2014

(87) PCT Pub. No.: WO2013/083137
PCT Pub. Date: Jun. 13, 2013

(65) Prior Publication Data
US 2014/0360896 A1    Dec. 11, 2014

(30) Foreign Application Priority Data

Dec. 9, 2011 (DK) .......................... PA 2011 70693

(51) Int. Cl.
*B65D 83/10* (2006.01)
*A61M 25/00* (2006.01)
*A61M 25/01* (2006.01)

(52) U.S. Cl.
CPC ....... *A61M 25/002* (2013.01); *A61M 25/0111* (2013.01); *A61M 2025/0046* (2013.01)

(58) Field of Classification Search
CPC .............. A61M 5/002; A61M 25/0111; A61M 2025/0046; A61B 19/026; B65D 81/24
USPC ........ 206/364, 210, 438, 205; 604/171, 172, 604/263, 265
See application file for complete search history.

(56) References Cited

U.S. PATENT DOCUMENTS 8,181,778 B1 * 5/2012 van Groningen ... A61M 25/002
                                                        206/210
2006/0196783 A1 * 9/2006 Bruun et al. .................. 206/210

FOREIGN PATENT DOCUMENTS

| CN | 201279336 Y | 7/2009 |
| EP | 2450076 A1 | 5/2012 |
| GB | 1493257 A | 11/1977 |
| RU | 2184573 C2 | 7/2002 |
| WO | 9811932 A1 | 3/1998 |
| WO | 2011019359 A1 | 2/2011 |

* cited by examiner

*Primary Examiner* — J. Gregory Pickett
*Assistant Examiner* — Rafael Ortiz
(74) *Attorney, Agent, or Firm* — Coloplast Corp., Coloplast A/S; Nick Baumann

(57) ABSTRACT

A package for a catheter is provided. The package includes a container with a first cavity and a second cavity. The cavities are configured so as to prevent liquid swelling medium stored in the container from travelling from the second cavity into the first cavity and out through an opening into the container. Thus, the position of the cavities with respect to each other allows them to function as a water-lock.

6 Claims, 2 Drawing Sheets

LIQUID STOP

The invention relates to a catheter package having a liquid stop so that liquid swelling medium is prevented from leaving the package.

BACKGROUND

Urinary catheter assemblies for draining the bladder are increasingly used for intermittent as well as indwelling or permanent catheterisation. Typically, urinary catheters are used by patients suffering from urinary incontinence or by disabled individuals like paraplegics or tetraplegics, who may have no control permitting voluntary urination and for whom catheterisation may be the way of urinating.

Urinary catheters are divided into two major groups of catheters, indwelling catheters and intermittent catheters. Indwelling catheters are typically inserted into the urethra and the bladder by medical personal (i.e. a trained professional, typically a nurse or physician) and has means for retaining the catheter inside the bladder for up to two weeks or more. Indwelling catheters are soft and flexible since they have to remain in the urethra for weeks. Indwelling catheters empty the bladder continuously. Intermittent catheters are typically inserted by the user him- or herself and sits only in the urethra and bladder for as long as it take to empty the bladder—e.g. for about 5-10 minutes. Intermittent catheters are used every 4-6 hours to empty the bladder corresponding roughly to the interval that people having no urinary problems will usually go to the bathroom. Intermittent catheters are typically more rigid than indwelling catheters since they have to be inserted by the user him-/herself and since they do not need to sit in the urethra for days or weeks. Intermittent urinary catheters may be provided with a hydrophilic coating that needs to be wetted prior to use and thereby absorbs a considerable amount of liquid. Ease of insertion is important for an intermittent catheter that has to be inserted several times a day. Such a hydrophilic coating will provide a very lubricious surface that has very low-friction when the catheter is to be inserted. Hydrophilic coated catheters, where the coating absorbs a considerable amount of liquid for a low frictious surface (swelling degree >100%), will not be suitable for indwelling catheters, because the hydrophilic surface coating would stick inside the mucosa of the urethra if left inside the body for a longer period, due to the hydrophilic coating transforming from being highly lubricious when fully wetted to being adhesive when the hydration level of the coating is reduced.

This invention relates to intermittent catheters with a hydrophilic coating of the kind that is wetted prior to use to absorb a considerable amount of liquid and to provide a very lubricious surface. Thus, the catheters may be stored in a package with the liquid swelling medium. When the package is positioned in a horizontal or inverted position the liquid swelling medium may spill from the package and wet the user's hands or clothes.

SUMMARY OF THE INVENTION

The invention concerns a package having a configuration of a first and a second cavity, so that the cavities function as a liquid stop, thereby preventing liquid swelling medium, stored in the first cavity, from spilling out of the package. The invention provides means for preventing spillage when the package is stored horizontally. The invention also provides means for preventing spillage when the package is turned upside-down. This may be particularly useful for people with poor hand dexterity, because they may accidentally knock the package over or drop it. The features of this invention prevent liquid swelling medium from spilling out of the package (or container) even if the container is knocked over.

DETAILED DESCRIPTION OF THE INVENTION

In a first aspect, the invention relates to a catheter package comprising
a container for accommodating a catheter and a liquid swelling medium
a hydrophilic coated catheter and a liquid swelling medium stored in the container
wherein the container defines a first cavity for storing the liquid swelling medium and a second cavity communicating with an opening into the container and the cavities are configured so as to prevent liquid from travelling from the first cavity into the second cavity when the catheter package is tilted horizontally or inverted.

By providing a catheter package as explained, it is avoided that the liquid swelling medium leaves the first cavity when the catheter package is in the horizontal position or even if the package is inverted. It is desirable to avoid that the liquid swelling medium leaves the cavity because the amount of the swelling medium may be reduced below the amount needed to activate the hydrophilic coating or maintain the hydrophilic coating activated. Furthermore, the liquid swelling medium may wet the user's hands or stain the clothes of the user, if it is spilled out of the package.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted. The same definitions apply to the package and container—the proximal end is the end storing the proximal end of the catheter and the distal end is the opposite end.

The longitudinal direction is defined as the direction from the distal to the proximal end. The transverse direction is the direction perpendicular to the longitudinal direction, which corresponds to the direction across the main tubular part of the catheter.

The catheter described in this application may be used as a urinary catheter for intermittent catheterisation.

The catheter comprises a main tubular part extending from the distal end to the proximal end. The tip is positioned in the proximal end of the catheter and is provided as a rounded, closed end of the main tubular part of the catheter. The catheter may comprise a connector in the distal end and may in an embodiment comprise a flared end of the catheter, so that the diameter of the connector increases in the distal direction with respect to the tubular part. The catheter may also comprise a handle in the distal end, which has a length allowing the user to manipulate the catheter.

Usually catheters used as urinary draining devices are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 18 FR corresponds to a catheter with an outer diameter of 6 mm.

Catheters of this invention are to be provided with a hydrophilic coating. The hydrophilic coating may be provided only on the insertable part of the catheter. The hydrophilic surface coating is of the kind which, when hydrated or swelled using a swelling medium, reduces the friction on the surface area of the catheter which is intended to be inserted into the urinary channel of a user corresponding to the insertable part of the catheter. Thus the hydrophilic coating needs to be activated at some point prior to use to be lubricious.

The catheter may be stored in pre-wetted condition or stored in an environment providing the conditions to activate the hydrophilic coating that is in contact with water or in a water-vapour saturated environment.

By horizontal position, referral is to the longitudinal direction of the catheter package is horizontal. Likewise, by vertical position the referral is to the longitudinal direction of the package being vertical.

By inverted is meant that the package has a defined opening allowing access to the catheter and that the package is placed in an upside-down vertical position so that the opening generally faces downwards. This corresponds to the distal end of the package facing generally downwards.

The container and cover may preferably be made of materials such as Poly Propylene (PP), Poly Ethylene (PE) including high density Poly Ethylene (HDPE), Cyclic Olefin Copolymer (COC), Poly Vinyl Chloride (PVC), Poly Vinylidene Chloride (PVDC), or fluoride polymers.

The length of the container may be in the range of 110-240 mm, such as in the range of 140-230 mm. Typically, the length of a container for a female catheter may be in the low end of the range, whereas the length of a container for a male catheter may be in the high end of the range. The diameter of the container may be in the range of 15-35 mm.

In an embodiment, the second cavity of the container defines an inner tube-element extending coaxially of the container inside the first cavity of the container.

The inner tube-element defining the second cavity has an inlet inside the first cavity—that is in the proximal end of the inner tube-element—where the inlet preferably is spaced from the inner surface of the first cavity. In an example, the diameter of the inner tube may be between 10 and 15 mm, so as to leave enough clearance around the catheter. In this case the inner diameter of the container may be more than 20 mm, so as to leave enough volume in the first cavity to prevent the liquid swelling medium from entering into the inlet of the second cavity.

In a related embodiment an inlet of the inner tube-element inside the first cavity defines a lip-valve.

A lip-valve assists in ensuring that the liquid swelling medium is prevented from entering into the second cavity.

In an embodiment, a first distance between an inner surface of the first cavity and an inner surface of the second cavity at the inlet thereof exceeds a second distance between an inner surface of the first cavity and the level of liquid swelling medium inside the first cavity when the package is stored horizontally.

When the relationship between the first distance and the second distance is as defined above, the liquid swelling medium will be prevented from entering into the second cavity and from there to the opening of the package, even when the package is stored horizontally.

The first distance is defined as the distance between an inner surface of the first cavity and an inner surface at the inlet of the second cavity, typically the distance perpendicular to the inlet. The second distance corresponds to the level of the liquid swelling medium inside the first cavity, when the package is stored horizontally.

In another embodiment, a third distance between an inner surface in the distal end of the first cavity and the inlet of the inner tube-element exceeds a fourth distance between an inner distal surface in the distal end of the first cavity and the level of liquid swelling medium inside the first cavity, when the package is stored vertically with the distal end facing downwards.

When the relationship between the third distance and the fourth distance is as defined above, the liquid swelling medium will be prevented from entering into the second cavity and from there to the opening of the package, even when the package is turned upside down—that is inverted so that the distal end of the package faces generally downwards in the vertical position.

The package may comprise a urine collecting bag that may be attached to the distal end of the catheter. Such a urine collecting bag alleviates the need for a toilet when the user has to catheterise. The urine collecting bag may be attached to the catheter (e.g. welded or adhered to the catheter)—or may be a separate element that is attachable to the catheter, when the catheter is to be used. The attachment may be done through a connecting piece or by adapting the size of the inlet of the urine collecting bag to fit to the distal end of the catheter. Both configurations (attached to or attachable to) lead to a catheter assembly in form of a set in which the urine collecting bag is able to communicate with the catheter and thereby collect the urine inside the collecting bag.

The urine collecting bag may be made of foil material, for example PE, and may be able to contain a volume of up to approximately 750 ml.

DETAILED DESCRIPTION OF THE DRAWING

Figure 1:
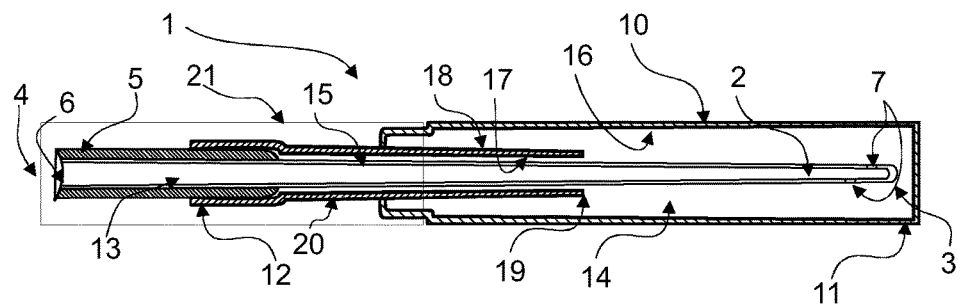
FIG. 1 illustrates a catheter package with a water lock according to the invention.

FIG. 1 illustrates a catheter package 1 according to the invention and including a catheter 2. The catheter 2 has a proximal end 3 adapted for insertion into a bodily canal—for example a urethra—and a distal end 4 with a handle 5 and an outlet 6 for e.g. urine. For letting urine enter into the inner lumen of the catheter, the catheter is in the illustrated embodiment provided with eyelets 7 in the proximal end 3.

The package 1 comprises a container 10 having a proximal end 11 and a distal end 12. The container 10 has an opening 13 in the distal end. The container is provided with a first cavity 14 and a second cavity 15. The liquid swelling medium is accommodated in the first cavity 14—see FIGS. 2-4. The catheter is accommodated in the first and second cavity. In the illustrated embodiment, the parts of the package are generally cylindrical and the cavities 14, 15 have inner surfaces 16, 17 defining the lumen of the cavities. Thus, in the illustrated embodiment, the second cavity 15 is provided as the inside of an inner tube-element 18 positioned partly inside the first cavity 14. Thus, as illustrated in this embodiment, the catheter 2 is longer than the inner tube 18. The second cavity 15 provided partly inside the first cavity 14 functions as a liquid stop. A liquid stop may also be known as a water-lock. The inner tube-element 18 has a proximal end 19 facing towards the proximal end 11 of the container. In the illustrated embodiment the inner tube-element 18 is formed as an integral part of the container 10. In the embodiment of FIG. 1, the container has an extension part 20 in the distal end, which has a reduced diameter compared to the part of the container having the first cavity 14. The distal end of the extension part 20 thus constitutes the opening 13 of the container. The extension part 20 also constitutes the distal end of the inner tube-element 18 with the second cavity 15. This means that the second cavity 15 communicates with the opening 13 of the container at the distal end 12 of the container. The handle 5 of the catheter and the extension part 20 of the container may have complementary means for detachably attaching the two parts together. The container 10 may be provided with a closure 21 for enclosing the catheter completely.

Figure 2:
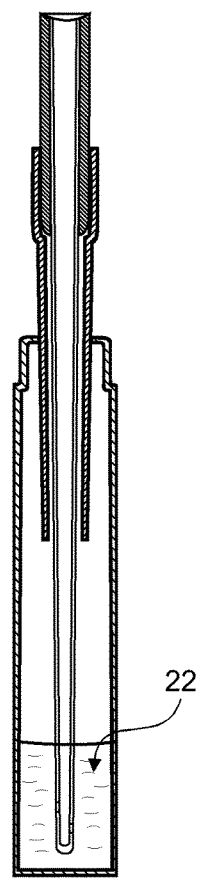
FIG. 2 illustrates the catheter package in vertical position and including liquid swelling medium.

In FIG. 2 the same embodiment is illustrated in a vertical position and illustrating liquid swelling medium 22 in the bottom of the container. The closure is removed in FIGS. 2 and 3.

Figure 3:
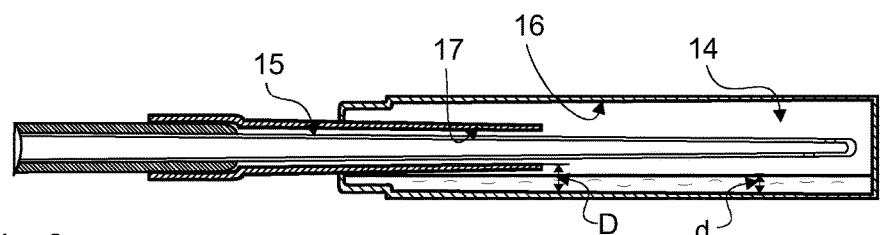
FIG. 3 illustrates the catheter package in a horizontal position and including liquid swelling medium.

In FIG. 3, the same embodiment is illustrated in a horizontal position. From the figure, it can be seen that the liquid swelling medium 22 is prevented from running out of the container 10 due to the position of the second cavity 15 with respect to the first cavity 14. The distance D between the inner surface 16 of the first cavity and the inner surface 17 of the second cavity is larger than the level d defined by the liquid swelling medium 22 contained in the container.

Figure 4:
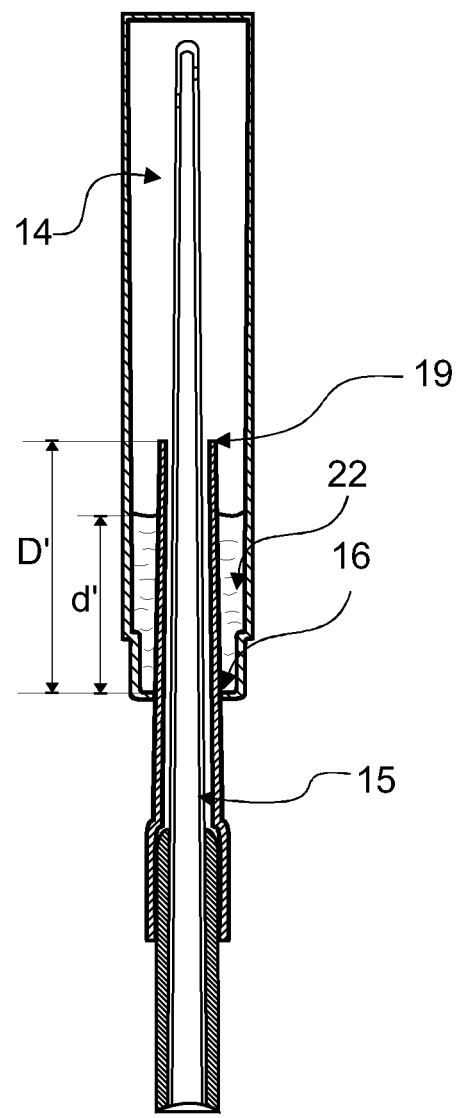
FIG. 4 illustrates the catheter package in an inverted upside-down position with the distal end of the package facing downwards.

In FIG. 4, the same embodiment is illustrated when it is turned upside down or inverted.

From the figure, it can be seen that the liquid swelling medium 22 is prevented from running out of the container 10 due to the relationship between the first and second cavity. The distance D' between the inner surface of the first cavity in the distal end and the proximal end of the inner tube element is larger than the level d' defined by the liquid swelling medium 22 contained in the container.

The invention claimed is:

1. A catheter package comprising:
    a container and an inner-tube element formed as an integral part of the container, the container containing a hydrophilic coated catheter, the hydrophilic coated catheter having a proximal end insertable into a urethra and a distal end provided with an outlet adapted to allow urine to exit the hydrophilic coated catheter, the container having a first cavity and a second cavity, with a portion of the inner-tube element extending coaxially inside of the first cavity of the container and with the second cavity formed by an inner surface of the inner-tube element, where the second cavity formed by the inner surface of the inner-tube element has a proximal opening located in the first cavity and a distal opening located at a distal end of the container, with the proximal end of the hydrophilic coated catheter extending out of the proximal opening of the second cavity and with the distal end of the hydrophilic coated catheter extending out of the distal opening of the second cavity;
    a closure coupled to the container; and
    a liquid contained in the first cavity of the container;
    wherein the closure is coupled to the container to completely enclose the hydrophilic coated catheter within the package;
    wherein the hydrophilic coated catheter is stored in the package in a pre-wetted condition where a hydrophilic coating of the hydrophilic coated catheter is wetted by the liquid contained in the first cavity of the container;
    wherein the inner-tube element and the first cavity are configured to prevent the liquid contained in the first cavity of the container from exiting the opening located at a distal end of the container.

2. The catheter package of claim 1, wherein a distance D is provided between an inner surface of the first cavity and the inner surface of the inner-tube element, and the distance D is selected to prevent the liquid from travelling from the first cavity into the second cavity when the catheter package is in a horizontal orientation.

3. The catheter package of claim 1, wherein the container is in a vertical position with the inner-tube element located distal of the proximal end of the hydrophilic coated catheter, and the liquid is in contact with the proximal end of the hydrophilic coated catheter and not in contact with the inner-tube element.

4. The catheter package of claim 1, wherein the container is in an inverted vertical position with the proximal end of the hydrophilic coated catheter located distal of the inner-tube element, and the liquid contained in the first cavity of the container is prevented from entering the inner-tube element.

5. A catheter package comprising:
    a hydrophilic coated catheter having a proximal end insertable into a urethra;
    a container and an inner-tube element formed as an integral part of the container, the container having a first cavity and a second cavity, with a portion of the inner-tube element extending inside of the first cavity of the container and with the second cavity formed by an inside of the inner-tube element, where the second cavity formed by the inside of the inner-tube element has a proximal opening located in the first cavity and a distal opening located at a distal end of the container, with the hydrophilic coated catheter extending through the inner-tube element and the proximal end of the hydrophilic coated catheter extending out of the proximal opening of the second cavity and into the first cavity;
    a closure coupled to the container; and
    a liquid contained in the first cavity of the container;
    wherein the closure is coupled to the container to completely enclose the hydrophilic coated catheter within the package;
    wherein the hydrophilic coated catheter is stored in the package in a pre-wetted condition where a hydrophilic coating of the hydrophilic coated catheter is wetted by the liquid contained in the first cavity of the container;
    wherein the inner-tube element and the first cavity are configured to prevent the liquid contained in the first cavity of the container from exiting the opening located at a distal end of the container.

6. A catheter package comprising:
    a hydrophilic coated catheter having a proximal end insertable into a urethra;
    a container and an inner-tube element formed as an integral part of the container, the container having a first cavity and a second cavity, with a portion of the inner-tube element extending inside of the first cavity of the container and with the second cavity formed by an inside of the inner-tube element, where the second cavity formed by the inside of the inner-tube element has a proximal opening located in the first cavity and a distal opening located at a distal end of the container, with the hydrophilic coated catheter extending through the inner-tube element and the proximal end of the hydrophilic coated catheter extending out of the proximal opening of the second cavity and into the first cavity;

a closure coupled to the container; and a liquid contained in the first cavity of the container;

wherein the closure is coupled to the container to completely enclose the hydrophilic coated catheter within the package;

wherein the hydrophilic coated catheter is stored in the package in a pre-wetted condition where a hydrophilic coating of the hydrophilic coated catheter is wetted by the liquid contained in the first cavity of the container;

wherein, when the closure is removed from the container, wherein the inner-tube element and the first cavity are configured to prevent the liquid contained in the first cavity of the container from exiting the opening located at a distal end of the container.

* * * * *